United States Patent
Kashid et al.

(10) Patent No.: US 8,048,449 B2
(45) Date of Patent: Nov. 1, 2011

(54) MOUTH DISSOLVING PHARMACEUTICAL COMPOSITION AND PROCESS FOR PREPARING THE SAME

(75) Inventors: Namdev Kashid, Sholapur (IN); Gour Mukherji, Gurgaon (IN)

(73) Assignee: Jubilant Organosys Ltd., Noida, Uttar Pradesh (IN)

( * ) Notice: Subject to any disclaimer, the term of this patent is extended or adjusted under 35 U.S.C. 154(b) by 278 days.

(21) Appl. No.: 12/097,813

(22) PCT Filed: Aug. 30, 2006

(86) PCT No.: PCT/IN2006/000319
§ 371 (c)(1),
(2), (4) Date: Jun. 17, 2008

(87) PCT Pub. No.: WO2007/074472
PCT Pub. Date: Jul. 5, 2007

(65) Prior Publication Data
US 2008/0317853 A1 Dec. 25, 2008

(30) Foreign Application Priority Data

Dec. 27, 2005 (IN) .......................... 3482/DEL/2005

(51) Int. Cl.
*A61K 9/20* (2006.01)
*A61K 31/167* (2006.01)
*A61K 31/551* (2006.01)
*A61K 31/4353* (2006.01)
*A61K 31/546* (2006.01)
*A61K 31/4545* (2006.01)

(52) U.S. Cl. ........ 424/465; 514/220; 514/629; 514/319; 514/222.5; 514/290

(58) Field of Classification Search ................... 424/465; 514/220, 629, 319, 222.5, 290
See application file for complete search history.

(56) References Cited

U.S. PATENT DOCUMENTS

| 5,178,878 A | 1/1993 | Wehling et al. |
|---|---|---|
| 5,188,825 A | 2/1993 | Iles et al. |
| 5,631,023 A | 5/1997 | Kearney et al. |
| 5,827,541 A | 10/1998 | Yarwood et al. |
| 5,976,577 A | 11/1999 | Green et al. |
| 6,024,981 A | 2/2000 | Khankari et al. |
| 6,221,392 B1 | 4/2001 | Khankari et al. |
| 6,740,339 B1 | 5/2004 | Ohkouchi et al. |
| 2002/0001617 A1 * | 1/2002 | Lee et al. ................ 424/465 |
| 2002/0071864 A1 | 6/2002 | Kim et al. |
| 2003/0175339 A1 | 9/2003 | Bunick et al. |
| 2003/0215502 A1 | 11/2003 | Pruss et al. |
| 2004/0171669 A1 | 9/2004 | Chenevier |
| 2005/0244343 A1 | 11/2005 | Witham et al. |

FOREIGN PATENT DOCUMENTS

| EP | 1166801 | 1/2002 |
|---|---|---|
| WO | WO9846213 | 10/1998 |
| WO | WO03030868 | 4/2003 |
| WO | WO2004066974 | 8/2004 |
| WO | WO2006058250 | 6/2006 |

* cited by examiner

*Primary Examiner* — Robert A Wax
*Assistant Examiner* — Aradhana Sasan
(74) *Attorney, Agent, or Firm* — Cozen O'Connor

(57) ABSTRACT

Disclosed herein is a orally disintegrating and/or dissolving oral pharmaceutical composition, comprising one or more active pharmaceutical ingredients, one or more fillers having particle size of 100 microns or above, a high and desirable amount of silicon dioxide, one or more disintegrating agents, optionally effervescent couple, wherein said composition has good organoleptic properties like desired mouth feel and fast oral disintegration time.

33 Claims, No Drawings

MOUTH DISSOLVING PHARMACEUTICAL COMPOSITION AND PROCESS FOR PREPARING THE SAME

PRIORITY CLAIM

This is a U.S. national stage of application No. PCT/IN2006/000319, filed on 30 Aug. 2006. Priority is claimed on the following application(s): Country: India, Application No.: 3482/DEL/2005, Filed: 27 Dec. 2005, the content of which is/are incorporated here by reference.

FIELD OF THE INVENTION

In general, this invention relates to the field of drug delivery system and in particular to an improved mouth dissolving pharmaceutical composition. More specifically, but without restriction to the particular embodiments hereinafter described in accordance with the best mode of practice, this invention provides a rapidly disintegrating and/or dissolving pharmaceutical composition having good organoleptic properties and method of making the same.

BACKGROUND OF THE INVENTION

Pharmaceutical compositions exist to optimize the delivery of a pharmaceutical active to its site of release. Compliance has become a major problem, particularly for pediatric and geriatric patients or certain patients who already have difficulty in swallowing solid medications. Oral liquid formulations such as suspension pharmaceutical compositions have been developed as an alternative to tablets in order to circumvent this problem; however, suspensions are often thermodynamically unstable and may result in aggregation and sedimentation during storage. Problems are often encountered because the accuracy of the dose depends on the even distribution of particles in the suspensions at the time the preparations are administered to the patients.

It is often desirable to have a tablet that disintegrates and disperses rapidly in the mouth without requiring any water intake other than the normal flow of saliva. Such tablets are easier for the elderly and children who often have difficulty in chewing or swallowing large capsules or tablets.

Patient convenience leads to compliance with the prescribed dosing regimen and, as a consequence, to enhanced therapeutic benefit. Orally disintegrating tablets are a viable alternative for convenient administration of drugs to patients who have difficulty in swallowing.

Rapidly disintegrating oral pharmaceutical compositions should have a pleasant taste, good mouth feel and should dissolve quickly. It is generally recognized that rapidly disintegrating tablets must dissolve in the mouth within 60 secs, more preferably in less than 30 secs. Besides, they can be taken at any time or place without the need for chewing or drinking water or any other liquid. When placed in mouth, these tablets disintegrate in a few seconds, resulting in quick absorption of the drug substances through the buccal and oesophageal mucosa, resulting in faster bioavailability of active ingredients with minimal first pass metabolism.

Widely known technologies that have been developed in the formulation of fast disintegrating tablets employ techniques of freeze-drying, direct compression and moulding.

Several fast dissolving/disintegrating drug delivery systems have been developed to assist pediatric and geriatric patients. Cardinal Healthcare markets Zydis™, which is a freeze-dried tablet (U.S. Pat. Nos. 4,642,903, 5,188,825, 5,631,023, 5,827,541 and 5,976,577) having an oral dissolution time of 2 to 5 seconds. The freeze-drying technology has limitations due to factors such as time, costly equipment and processing conditions. Besides, tablets formulated by this technology lack physical resistance and heed special handling and packaging.

Cima labs markets Orasolv™ (U.S. Pat. No. 5,178,878) and Durasolv™ (U.S. Pat. Nos. 6,221,392 and 6,024,981) where Orasolv™ is an effervescent direct compression tablet, that disperses in mouth's saliva with the aid of almost hardly noticeable effervescence and dissolves in less than one minute, leaving the coated drug powder. The unpleasant flavor of the drug is addressed by coating of the drug powder and effervescence. The major disadvantage of Orasolv™ is its mechanical strength due to light compression. Durasolv™ is a recently introduced direct compression tablet having higher mechanical strength than Orasolv™ due to the use of higher compaction pressures during tabletting.

U.S. Patent Application No. 20030175339 to Bunick, Frank, J.; et al. discloses a process for preparing chewable or disintegrable tablet comprising an active, a hydrate and a water-swellable excipient (disintegrant). The process comprises applying energy (heat) to tablets to achieve softening effect. It also discloses the preparation of tablets by direct compression. The tablets have a friability of less than 2%.

U.S. Patent Application No. 20050019398 to Kothari, Sanjeev; et al. discloses granules for preparing flash-melt oral pharmaceutical compositions. The formulation comprises a super disintegrant, a dispersing agent, a distributing agent and a binder. The disclosed composition optionally contains sweetening and flavouring agents. The reference discloses that the granules are prepared without the aid of solvents and are stable. Said application also discloses that the tablets disintegrate in mouth under 25 seconds. Calcium silicate is used as the dispersing agent.

Generally mannitol is commonly used as an excipient (diluent) in the manufacture of rapidly disintegrating pharmaceutical compositions because of its negative heat of solution and sweetness. According to Khankari et al. (U.S. Pat. No. 6,221,392 and U.S. Pat. No. 6,024,981) the use of directly compressible mannitol with large particle size in rapidly disintegrating pharmaceutical compositions presents problems since they do not solubilize quickly. This contributes to a mouth sensation of gritty or sandy texture of the mannitol as the pharmaceutical composition disintegrates. Khankari et al. have adopted the process of incorporating non-directly compressible fillers, including mannitol, which have fine particle size. By suitable adjustments in composition properties like flow and compressibility, Khankari et al, have been able to produce tablets by direct compression also.

None of the described prior art teaches a solution for the problems related to the use of filler like mannitol having large particle size where the problem is organoleptic characteristic like mouth feel due to the gritty or sandy texture of the filler, when prepared by a compression method.

It is, therefore, an object of the present invention to improve upon limitations in the prior art. Accordingly, the present invention provides an improved orally dissolving pharmaceutical formulation, which is able to dissolve rapidly in the mouth of the patient, with minimum of grit or other organoleptic unpleasant sensations.

SUMMARY OF THE INVENTION

It is a principal object of the present invention to provide an improved orally disintegrating and/or dissolving pharmaceutical composition, wherein said pharmaceutical composition provides good organoleptic properties like good mouth feel and fast oral disintegration time.

Another object of the present invention is to provide an improved rapidly/orally disintegrating or dissolving oral pharmaceutical composition, which is able to dissolve in about 60 seconds or less in the patient's mouth.

Further object of the present invention is to provide an improved orally disintegrating or dissolving pharmaceutical composition, said pharmaceutical composition having minimum grit or sandy effect.

Another object of the present invention is to provide an improved orally disintegrating or dissolving pharmaceutical composition, wherein said composition employs a desirable quantity of silicon dioxide, which provides better cushioning effect to the composition and hence quicker dissolution and smoother mouth feel when swallowed.

The following embodiments further describe the objects of the present invention in accordance with the best mode of practice, however, disclosed invention is not restricted to the particular embodiments hereinafter described.

In accordance with one preferred embodiment, the present invention provides an improved orally disintegrating or dissolving pharmaceutical composition, wherein said pharmaceutical composition is a tablet formulation. The formulation comprises one or more active ingredient, one or more fillers, a desirable amount of silicon dioxide acting as cushioning agent and other pharmaceutically acceptable excipients.

In accordance with another embodiment of the present invention, said formulation comprises one or more active ingredients, one or more fillers having large particle size, preferably mannitol, other pharmaceutically acceptable excipients along with high and desirable amount of silicon dioxide, preferably colloidal or amorphous silicon dioxide, which provides better cushioning effect between the used filler particles and hence quicker dissolution and smoother mouth feel when swallowed.

In accordance with still another embodiment of the present invention, said formulation comprises one or more active ingredients, mannitol having particle size of 100-450 microns or above, colloidal and/or amorphous silicon dioxide in an amount of about 3 to 30% by weight, one or more disintegrating agents and optionally effervescent couple. The pharmaceutical composition also includes other conventional excipients like disintegrants, surfactants, flavouring aids, lubricants, sweeteners, glidants, antiadherants or mixtures thereof. Unless otherwise stated, the percentage compositions mentioned herein refer to percentages of the total weight of the final composition or formulation. For purpose of present invention composition and formulation should be given the same meaning.

In accordance with still another embodiment of the present invention, said formulation comprises one or more active ingredients, mannitol having average particle size of 100 microns to 450 microns, preferably 150 to 350 microns, colloidal and/or amorphous silicon dioxide in an amount of preferably about 5 to 30% by weight, most preferred is 5 to 15%, one or more disintegrating agents and optionally effervescent couple. The pharmaceutical composition also includes other conventional excipients like disintegrants, surfactants, flavouring aids, lubricants, anti-adherents, glidants, sweeteners and mixtures thereof. These conventional excipients are used in the present invention in an amount of about 10%.

In accordance with another embodiment of the present invention, there is provided a process for preparing an orally disintegrating and/or dissolving pharmaceutical composition comprising the steps of:

(a) preparing granules of an active ingredient along with silicon dioxide and appropriate quantities of conventional excipients, wherein the amount of silicon dioxide is about 5 to 30% by weight;
(b) granules as obtained in step (a) are mixed with the filler and appropriate quantities of conventional excipients, wherein the particle size of filler is 150 microns or above and the filler is in the directly compressible, granulated, compacted or agglomerated form;
(c) compressing the blend as obtained in step (b) to form orally disintegrating and/or dissolving tablets.

It will be appreciated by those skilled in the art that composition of the present invention can also be converted into other dosage forms like dispersible tablets, granules and sachet containing such granules.

DETAILED DESCRIPTION OF THE INVENTION

While this specification concludes with claims particularly pointing out and distinctly claiming that, which is regarded as the invention, it is anticipated that the invention can be more readily understood through reading the following detailed description of the invention and study of the included examples.

In mouth dissolving or orally disintegrating tablet formulations, palatability and smooth mouth feel is one of the essential properties of a rapidly disintegrating or dissolving oral pharmaceutical composition, which is interrelated with patient compliance that results in enhanced therapeutic benefit. The role of excipients is important in the formulation of rapidly dissolving oral tablets. The excipients when incorporated in the formulation, impart the desired organoleptic properties and product efficacy.

The present invention relates to a rapidly/orally disintegrating or dissolving oral pharmaceutical composition, comprising one or more active ingredients, one or more fillers having particle size of 100-450 micron or above, a high amount of colloidal and/or amorphous silicon dioxide as cushioning agent, one or more disintegrating agents, optionally effervescent couple said composition having good organoleptic properties like fast oral disintegration time and desired mouth feel.

"Rapidly or orally disintegrating/dissolving" in accordance with the present invention, means that the tablet disintegrates or disperses preferably within 60 seconds or less, most preferably within 30 seconds or less.

"Desired mouth feel" in accordance with the present invention means the pharmaceutical composition disintegrates in the mouth with a smooth feeling and with a minimum of unpleasant grittiness, sandy or chalky feeling.

"Average particle size" in accordance with the present invention means volume mean diameter of a sample of any ingredient in which 50% of the sample is below and above that size.

"Active pharmaceutical agents" in accordance with the present invention means any pharmaceutical ingredients or their pharmaceutical acceptable salts, derivatives, solvates or hydrates which elicit desired therapeutic response of any therapeutic category and is useful for the formulation of rapidly or orally disintegrating oral pharmaceutical compositions.

In one embodiment the active pharmaceutical ingredients for the pharmaceutical composition of the present invention can be water-soluble or water insoluble. For the purpose of the invention water-soluble active pharmaceutical ingredients are those, which require less than 100 parts of solvent to dissolve 1 part of active pharmaceutical ingredient, whereas water-insoluble active pharmaceutical ingredients are those, which require more than 100 parts of solvent to dissolve 1 part of active pharmaceutical ingredient. The preferred active pharmaceutical agents contemplated for the present invention include but are not limited to olanzapine, risperidone, loperamide, loratadine, hydrochlorothiazide, donepezil hydrochloride, ondansetron, clonazepam, clozapine, mitrazapine, oxcarbazepine, tramadol, cetirizine, lamotrizine, alprazolam, rizatriptan, zolmitriptan, montelukast, desloratadine and paracetamol.

The filler(s) used in the composition of the present invention are polyols or related compounds. Suitable examples of polyols include but are not limited to mannitol, dextrates, NF hydrated (Emedex™), sorbitol, xylitol, sucrose, fructose, lactitol, erythritol or maltitol. Said polyols have particle texture that is crystalline or amorphous or agglomerate in nature. The most preferred polyol is mannitol in amount of preferably 30-80% by weight having large particle size of 100-450 micron. Preferably average particle size of mannitol for the present invention is 150-350 micron. Mannitol is commercially available from manufacturer Roquette, France, under different brand names like Pearlitol 160C, Pearlitol 200 DC, Pearlitol 300 DC, Pearlitol 400 DC and Pearlitol 500DC. Pearlitol 160C has average particle size of 160 microns. Similarly Pearlitol 300DC, 400 DC and 500DC have mean particle diameter of 250, 360 and 520 microns, respectively. Mannitol is also available commercially under the brand name Pearlitol SD 200 and Pearlitol SD 300. All of the above mentioned different types of mannitols are contemplated for pharmaceutical composition of the present invention.

In addition there is cushioning agent namely colloidal and/or amorphous silicon dioxide, which is used in significantly higher proportion (greater than 3%) as compared to the normally used amounts (around 1%) for tablet lubrication. Large particles or crystals of mannitol get fused together during compression forming strong bonds at the lines of fusion. These compressed mannitol particles tend to dissolve slowly and being in compacted state give coarse mouthfeel when ingested as a mouth-dissolving tablet. Presence of high amount of colloidal and/or amorphous silicon dioxide in the tablet gives a sandwich or cushioning effect between the mannitol particles, resulting in weaker particle-particle interactions on compression and hence, quicker dissolution and smoother mouthfeel when swallowed.

It is found, surprisingly, that addition of high amount of colloidal and/or amorphous silicon dioxide covers the surface of filler, thus, improves or completely masks the gritty or sandy mouth feel due to the filler without affecting the mouth disintegration of the pharmaceutical composition as the disintegration time of the pharmaceutical composition is less than 60 seconds. Further, colloidal and/or amorphous silicon dioxide provides hydrophilicity in the matrix, which improves the disintegration of the rapidly disintegrating pharmaceutical composition of the present invention. The use of high amount (5% to 30%) of colloidal or amorphous silicon dioxide imparts more hydrophilic and cushioning properties between the crystalline mannitol, which improves the mouth feel.

Colloidal silicon dioxide is commercially available from three different sources under different brand names like Aerosil® from Degussa, Germany; Cab-O-Sil® from Cabot Corporation, and Wacker HDK from Wacker-Chemie GmbH. Similarly amorphous silicon dioxide is commercially available from J. M. Huber Corporation USA under the brand name RxCIPIENTS® GL200. Amorphous silicone dioxide is also commercially available as Syloid® 244 FP from Grace GmbH Germany. All of the above-mentioned brands of colloidal silicon dioxide and amorphous silicon dioxide are contemplated for the pharmaceutical composition of the present invention.

The pharmaceutical composition of the present invention also includes other conventional excipients like disintegrants, surfactants, flavoring aids, lubricants, sweeteners, glidants, antiadherants and mixtures thereof, which affect the elegancy and performance of the rapidly disintegrating oral pharmaceutical compositions. The additional excipients used in said formulation are present in small amounts, e.g. generally less than 10%, preferably 5% of the total mass of the tablet.

The lubricant is used herein as an additional excipient that can affect the performance of an orally disintegrating pharmaceutical composition. Suitable examples of lubricants include but are not limited to talc, sodium stearyl fumarate (Pruv), calcium stearate, magnesium stearate, zinc stearate, glyceryl behenate, stearic acid and glyceryl monostearate. Preferred lubricant for the composition of the present invention is sodium stearyl fumarate or magnesium stearate or combination thereof. Preferably the lubricant (s) of the present invention are employed in an amount of about 1 to 5% by weight.

Optional effervescent couple of the present invention includes compounds, which evolve gas. The preferred effervescent couple evolves gas by means of a chemical reaction between soluble acid source, an alkali monohydrogencarbonate or other carbonate source and water and/or saliva in the mouth. The gas produced by such a chemical reaction is carbon dioxide. The acid source may be any which are safe for human consumption and may include edible acids, such as, for example citric acid, tartaric acid, malic acid, fumaric acid, adipic acid, succinic acid and the like. Carbonate source includes dry solid carbonate and bicarbonate salts for example sodium carbonate, sodium hydrogen carbonate, magnesium carbonate, calcium carbonate and the like. The preferred effervescent couple for the present invention is citric acid (anhydrous)/sodium hydrogen carbonate. Preferably the effervescent couple is employed in an amount of about 10 to 30% by weight.

The disintegrant(s) used in the present invention may be selected from the group comprising of water soluble, water insoluble or water swellable materials which account for their disintegrating ability. Suitable disintegrants for the pharmaceutical composition of the present invention include but are not limited to microcrystalline cellulose (available commercially under the brand name Avicel® from FMC Biopolymer), croscarmellose sodium (commercially available from FMC Biopolymer under the brand name Ac-Di-Sol®), crosslinked polyvinylpyrrolidone (commercially available as Kollidon CL, Kollidon CL-M from BASF Pharma and Polyplasdone® XL, XL-10, from ISP Pharma Technologies), sodium starch glycolate (commercially available as Primogel® from DMV International and Explotab® from JRS Pharma), prolacrilin potassium (commercially available as Amberlite® IRP-88), pregelatinized starch (commercially available from colorcon under the brand name starch1500) and low substituted hydroxypropyl cellulose (L-HPC). The preferred disintegrant(s) for the composition of the present invention are crosslinked polyvinylpyrrolidone or polacrilin potassium or combination thereof. Preferably the disintegrant(s) of the present inventions are employed in an amount of about 10 to 30% by weight.

Suitable flavouring aid (s) used in the composition of present invention include but are not limited to strawberry, cherry, peppermint, black currant and caramel. Preferable flavoring aid is strawberry or cherry or orange or combination thereof. Preferably the flavoring aids of the present inventions are used in an amount of about 1 to 5% by weight.

Suitable surfactants for the composition of the present invention include but are not limited to sodium lauryl sulphate, polysorbate 80, polysorbate 60, polysorbate 40, polysorbate 20, poloxamers, and glyceryl monostearate. The preferred surfactant is sodium lauryl sulphate. Preferably the surfactants of the present inventions are used in an amount of about 1 to 4% by weight.

Suitable sweeteners include, for example, aspartame (Nutra sweet), saccharin and salts thereof, acesulfame potassium, sucralose, sucrose, fructose and the like. The preferred sweetener is aspartame (Nutra sweet). Preferably the sweeteners of the present invention are used in an amount of about 1 to 5% by weight.

Suitable anti-adherant and glidant of the present invention include but are not limited to talc, magnesium silicate, colloidal silicon dioxide, amorphous silicon dioxide and calcium silicate. Preferable glidants and antiadherants are amorphous silicon dioxide, colloidal silicon dioxide or combination thereof. Preferably anti-adherant and glidant are used in an amount of about 0.5-2% by weight.

The process for preparing an orally disintegrating and/or dissolving pharmaceutical composition of the present invention comprises the steps of:

(a) preparing granules of an active ingredient along with dioxide and appropriate quantities of conventional excipients, wherein the amount of silicon dioxide is about 5 to 30% by weight;

(b) granules as obtained in step (a) are mixed with the filler and appropriate quantities of conventional excipients, wherein the particle size of filler is 150 microns or above and the filler is in the directly compressible, granulated, compacted or agglomerated form;

(c) compressing the blend as obtained in step (b) to form orally disintegrating and/or dissolving tablets.

The pharmaceutical composition of the present invention is prepared by employing preferably wet granulation technique. However, the process is not limited to wet granulation and other forms of processing, like, direct compression or dry granulation, may also be adopted.

The following non-limiting examples illustrate specific embodiments of the present invention. They are, however, not intended to be limiting the scope of the present invention in any way.

Example 1

Paracetamol rapidly/orally disintegrating/dissolving tablet: Composition:

| Sr. No. | Ingredients | Quantity in mg |
|---|---|---|
| 1. | Paracetamol | 5 |
| 2. | Colloidal silicon dioxide (Aerosil 200) | 9 |
| 3. | Sodium stearyl fumarate (Pruv) | 3 |
| 4. | Crospovidone (Polyplasdone XL-10) | 17.5 |
| 5. | Aspartame (Nutra sweet) | 2 |
| 6. | Sodium lauryl sulfate | 0.9 |
| 7. | Peppermint flavor | 0.6 |
| 8. | Black currant flavor | 0.4 |
| 9. | Purified water* | q.s |
| 10. | Dextrates NF hydrated (Emdex) | 69.1 |
| 11. | Citric acid (anhydrous) | 1.5 |
| 12. | Fumaric acid | 3.0 |
| 13. | Sodium hydrogen carbonate | 8.0 |
| | Total | 120 |

*Evaporates during processing

Preparation Method:

1. Paracetamol (5 mg), colloidal silicon dioxide (8 mg), sodium stearyl fumarate (2 mg), crospovidone (7.5 mg) and aspartame (2 mg) were weighed and passed through 80 mesh sieve screen and were blended for 5-10 minutes.
2. The powder blend obtained from step (1) was granulated with sodium lauryl sulfate solution in water to obtain wet mass.
3. The wet mass of step (2) were passed through 20 mesh sieve screen and dried at suitable temperature between 40-65° C.
4. The dried granules of step (3) were passed through 40 mesh sieve screen.
5. Peppermint flavor (0.6 mg), black currant flavor (0.4 mg), citric acid (1.5 mg), fumaric acid (3 mg), sodium hydrogen carbonate (8 mg), colloidal silicon dioxide (1 mg), sodium stearyl fumarate (1 mg), crospovidone (10 mg) were sifted through 80 mesh sieve screen.
6. Dextrates NF hydrated (Emdex) was sifted through 50 mesh sieve screen and mixed with step (5) ingredients.
7. Blend obtained in step (6) was further blended with drug granules as obtained in step (4).
8. The lubricated blend of step (7) was compressed to tablets using suitable punches.

Tablets were compressed using rotary compression machine. The resulting tablets had hardness of about 6 to 7 N and the friability was 1.2%. The average in vitro disintegration time was 14-15 seconds and in vivo disintegration time was 20-24 seconds.

Example 2

Olanzapine rapidly/orally disintegrating/dissolving tablet: Composition:

| Sr. No. | Ingredients | Quantity in mg |
|---|---|---|
| 1. | Olanzapine | 5 |
| 2. | Colloidal silicon dioxide (Aerosil 200) | 4 |
| 3. | Macrocrystalline cellulose (Avicel PH 112) | 10 |
| 4. | Sodium stearyl fumarate (Pruv) | 3 |
| 5. | Polacrilin potassium (Amberlite IRP 88) | 10 |
| 6. | Aspartame (Nutra sweet) | 1.5 |
| 7. | Sodium lauryl sulfate | 0.35 |
| 8. | Mannitol (Pearlitol SD 200) | 56.15 |
| 9. | Mannitol (Pearlitol SD 300) | 30.00 |
| | Total | 120 |

Preparation Method

1. Olanzapine and colloidal silicon dioxide were mixed and sifted through 80 mesh sieve screen.
2. Microcrystalline cellulose, sodium stearyl fumarate, aspartame, polacrilin potassium, sodium lauryl sulfate, mannitol (Pearlitol SD 200) were sifted through 80 mesh sieve screen and blended together.

3. The powder blend obtained form step (1) & (2) were further sifted through 80 mesh sieve screen.
4. Mannitol (Pearlitol SD 300) was sifted through 50 mesh sieve screen.
5. The powder blend obtained form step (3) & (4) were further blended and used for making tablets.

Tablets were compressed using rotary compression machine. The resulting tablets had hardness of about 6 to 8 N and the friability was 0.47%. The average in vitro disintegration time was 6-8 seconds.

Example 3

Donepezil Hydrochloride rapidly/orally disintegrating/dissolving tablet.
Composition:

| Sr. No. | Ingredients | Quantity in mg |
|---|---|---|
| 1. | Donepezil hydrochloride | 5.00 |
| 2. | Colloidal silicon dioxide (Aerosil 200) | 6.00 |
| 3. | Sodium stearyl fumarate (Pruv) | 3.00 |
| 4. | Crospovidone (Polyplasdone XL-10) | 16.00 |
| 5. | Aspartame (Nutra sweet) | 2.00 |
| 6. | Sodium lauryl sulfate | 1.00 |
| 7. | Strawberry flavor | 1.00 |
| 8. | Purified water* | q.s |
| 9. | Mannitol (Pearlitol 300 DC) | 26.00 |
| | Total | 60 |

*Evaporates during processing

Preparation Method:
1. Donepezil (5 mg), colloidal silicon dioxide (5 mg), sodium stearyl fumarate (2 mg), crospovidone (10 mg) and aspartame (2 mg) were weighed and passed through 80 mesh sieve screen and were blended for 5-10 minutes.
2. The powder blend obtained from step (1) was granulated with 4% aqueous solution of sodium lauryl sulfate to obtain wet mass.
3. The wet mass of step (2) was dried at suitable temperature between 40-65° C.
4. The dried granules of step (3) were passed through 40 mesh sieve screen.
5. Mannitol (Pearlitol 300DC) was sifted through 50 mesh sieve screen.
6. Strawberry flavor and remaining quantity of colloidal silicon dioxide (1 mg), sodium stearyl fumarate (1 mg) and crospovidone (6 mg) were weighed and passed through 80 mesh sieve screen and blended together.
7. The blend from step (6) was mixed with step (5) mannitol (Pearlitol 300DC).
8. The blend from step (7) was further blended with dried granules obtained from step (4) to obtain lubricated blend.
9. The lubricated blend of step (8) was compressed to tablets using suitable punches.

Tablets were compressed using rotary compression machine. The resulting tablets had hardness of about 6 to 7 N and the friability was 1.2%. The average in vitro disintegration time was 8-10 seconds.

Example 4

Hydrochlorothiazide rapidly/orally disintegrating/dissolving tablet:
Composition:

| Sr. No. | Ingredients | Quantity in mg |
|---|---|---|
| 1. | Hydrochlorothiazide | 12.5 |
| 2. | Colloidal silicon dioxide (Aerosil 200) | 11.5 |
| 3. | Sodium stearyl fumarate (Pruv) | 5.5 |
| 4. | Crospovidone (Polyplasdone XL-10) | 30.0 |
| 5. | Aspartame (Nutra sweet) | 2.0 |
| 6. | Sodium lauryl sulfate | 2.0 |
| 7 | Polyvinylpyrrolidone (PVP K 30) | 5.0 |
| 8. | Strawberry flavor | 1.0 |
| 9. | Purified water* | q.s |
| 10. | Mannitol (Pearlitol 300 DC) | 50.50 |
| | Total | 120.00 |

*Evaporates during processing

Preparation Method
1. Hydrochlorothiazide (12.5 mg), colloidal silicon dioxide (10 mg), sodium stearyl fumarate (4 mg), crospovidone (20 mg) and aspartame (2 mg) were weighed and passed through 60 mesh sieve screen and were blended for 5-10 minutes.
2. The powder blend obtained from step (2) was granulated with solution of sodium lauryl sulfate and polyvinylpyrrolidone in water to obtain wet mass.
3. The wet mass of step (2) was dried at suitable temperature between 40-65° C.
4. The dried granules of step (3) were passed through 30 mesh sieve screen.
5. Mannitol (Pearlitol 300 DC) was sifted through 50 mesh sieve screen.
6. Strawberry flavor (1 mg) and remaining quantity of colloidal silicon dioxide (1.5 mg), sodium stearyl fumarate (1.5 mg) and crospovidone (10 mg) were weighed and passed through 80 mesh sieve screen and blended together.
7. The blend from step (6) was mixed with step (5) mannitol (Pearlitol 300DC).
8. The blend from step (7) was further blended with dried granules obtained from step (4) to obtain lubricated blend.
9. The lubricated blend of step (8) was compressed into tablets using suitable punches.

Tablets were compressed using rotary compression machine. The resulting tablets had hardness of about 7 to 9 N and the friability was 1.30%. The average in vitro disintegration time was 10-12 seconds.

Example 5

Olanzapine rapidly/orally disintegrating/dissolving tablet:
Composition:

| Sr. No. | Ingredients | Quantity in mg |
|---|---|---|
| 1. | Olanzapine | 5.03 |
| 2. | Amorphous silicon dioxide (RxCIPIENTS GL 200). | 5.00 |
| 3. | Sodium stearyl famarate (Pruv) | 2.50 |
| 4. | Crospovidone (Polyplasdone XL-10) | 17.97 |
| 5. | Aspartame (Nutrasweet) | 2.00 |
| 6. | Sodium lauryl sulfate | 1.00 |
| 7. | Talc | 0.50 |
| 8. | Strawberry flavor | 0.50 |
| 9. | Purified water* | q.s. |
| 10. | Mannitol (Pearlitol 160C) Granules** | 25.50 |
| | Total | 60 |

*Evaporates during processing.
**Preparation of mannitol (Pearlitol 160 C) granules:
a) Small quantity of Pearlitol 160C was dissolved in water,
b) Pearlitol 160C was sifted through 80 mesh sieve screen and loaded into 2 L RMG,
c) the material in RMG was granulated with step 1 solution,
d) granules obtained in step (c) were dried in tray drier for 1 hour (loss on drying 0.42%),
e) granules obtained in step (d) were dried milled through 25 mesh sieve screen.

Preparation Method

1. Olanzapine (5 mg), amorphous silicon dioxide (5 mg), sodium stearyl fumarate (2 mg), crospovidone (10 mg) and aspartame (2 mg) were weighed and passed through 60 mesh sieve screen and were blended for 5-10 minutes.
2. The powder blend obtained from step (1) was granulated using 14% aqueous solution of sodium lauryl sulfate to obtain wet mass.
3. The wet mass of step (2) was dried at suitable temperature between 40-65° C.
4. The dried granules of step (3) were passed through 30 mesh sieve screen.
5. The granules from step (4) were dry granulated and the resulting granules sifted through 25 mesh sieve screen.
6. Talc, strawberry flavor, remaining quantity of sodium stearyl fumarate (0.5 mg) and crospovidone (7.97 mg) were weighed and passed through 80 mesh sieve screen and blended with mannitol (Pearlitol 160 C) granules.
7. The blend from step (6) was further blended with dried granules obtained from step (5) to obtain lubricated blend.
8. The lubricated blend of step (7) was compressed to tablets using suitable punches.

Tablets were compressed using rotary compression machine. The resulting tablets had hardness of about 5 to 7 N and the friability was 1.32%. The average in vitro disintegration time was 6-7 seconds.

Example 6

Loratadine rapidly/orally disintegrating/dissolving tablet:
Composition:

| Sr. No. | Ingredients | Quantity in mg |
|---|---|---|
| 1. | Loratadine | 10.00 |
| 2. | Colloidal silicon dioxide (Aerosil 200) | 11.50 |
| 3. | Sodium stearyl fumarate (Pruv) | 4.50 |
| 4. | Crospovidone (polyplasdone XL-10) | 30.00 |
| 5. | Aspartame (Nutra sweet) | 2.00 |
| 6. | Sodium lauryl sulfate | 1.00 |
| 7. | Strawberry flavor | 1.50 |
| 8. | Purified water* | q.s. |
| 9. | Mannitol (Pearlitol 300 DC) | 58.50 |
| | Total | 120.00 |

*Evaporates during processing.

Preparation Method:

1. Loratadine (10 mg), colloidal silicon dioxide (8 mg), were weighed and passed through 80 mesh sieve screen and blended for 5-10 minutes.
2. Sodium stearyl fumarate (3 mg), crospovidone (20 mg) and aspartame (2 mg) were weighed and passed through 80 mesh sieve screen and blended for 5-10 minutes.
3. Blend from step (1) & (2) was mixed and sifted through 80 mesh sieve screen.
4. The powder blend obtained from step (3) was granulated with 4% aqueous solution of sodium lauryl sulfate to obtain wet mass.
5. The wet mass of step (4) was dried at suitable temperature between 40-65° C.
6. The dried granules of step (5) were passed through 40 mesh sieve screen.
7. Mannitol (Pearlitol 300DC) was sifted through 50 mesh sieve screen.
8. Strawberry flavor and remaining quantity of colloidal silicon dioxide (1.5 mg), sodium stearyl fumarate (1.5 mg) and crospovidone (10 mg) were weighed and passed through 80 mesh sieve screen and blended together.
9. The blend from step ((8) was mixed with step (7) mannitol (Pearlitol 300DC)
10. The blend from step (9) was further blended with dried granules obtained from step (6) to obtain lubricated blend.
11. The lubricated blend of step (10) was compressed into tablets using suitable punches.

Tablets were compressed using rotary compression machine. The resulting tablets had hardness of about 7 to 8 N and the friability was 0.95%. The average in vitro disintegration time was 10-15 seconds.

Example 7

Olanzapine rapidly/orally disintegrating/dissolving tablet:
Composition:

| Sr. No. | Ingredients | Quantity in mg |
|---|---|---|
| 1. | Olanzapine | 5.00 |
| 2. | Colloidal silicon dioxide (Aerosil 200) | 5.50 |
| 3. | Sodium stearyl fumarate (Pruv) | 2.50 |

-continued

Olanzapine rapidly/orally disintegrating/dissolving tablet:
Composition:

| Sr. No. | Ingredients | Quantity in mg |
|---|---|---|
| 4. | Crospovidone (Polyplasdone XL-10) | 14.00 |
| 5. | Aspartame (Nutra sweet) | 2.00 |
| 6. | Sodium lauryl sulfate | 0.50 |
| 7. | Strawberry flavor | 0.50 |
| 8. | Purified water* | q.s. |
| 9. | Mannitol (Pearlitol 300 DC) | 30.00 |
|  | Total | 60.00 |

*Evaporates during processing.

Preparation Method:
1) Olanzapine (5 mg), colloidal silicon dioxide (5 mg), sodium stearyl fumarate (2 mg), crospovidone (10) and aspartame (2 mg) were weighed and passed through 60 mesh sieve screen and were blended for 5-10 minutes.
2) The powder blend obtained from step (1) was granulated with 4% aqueous solution of sodium lauryl sulfate in water to obtain wet mass.
3) The wet mass of step (2) was dried at suitable temperature between 40-65° C.
4) The dried granules of step (3) were passed through 40 mesh sieve screen.
5) Mannitol (Pearlitol 300DC) was sifted through 50 mesh sieve screen.
6) Strawberry flavor and remaining quantity of colloidal silicon dioxide (0.5 mg), sodium stearyl fumarate (0.5 mg) and crospovidone (4 mg) were weighed and passed through 80 mesh sieve screen and blended together.
7) The blend from step (6) was mixed with step (5) mannitol (Pearlitol 300DC).
8) The blend from step (7) was further blended with dried granules obtained from step (4) to obtain lubricated blend.
9) The lubricated blend of step (8) was compressed to tablets using suitable punches.

Tablets were compressed using rotary compression machine. The resulting tablets had hardness of about 6 N and the friability was 1.060%. The average in vitro disintegration time was 4 seconds.

INDUSTRIAL APPLICATION OF THE INVENTION

The drug delivery technology of the present invention would be applicable for active ingredient of choice wherein the desired effect is a fast-dissolve on the tongue without the addition of liquid.

While this invention has been described in detail with reference to certain preferred embodiments, it should be appreciated that the present invention is not limited to those precise embodiments. Rather, in view of the present disclosure, which describes the current best mode for practicing the invention, many modifications and variations would present themselves to those skilled in the art without departing from the scope, and spirit of this invention.

We claim:
1. An orally disintegrating compressed tablet composition comprising:
(a) an active pharmaceutical agent;
(b) a filler having an average particle size of 150 microns or above, in an amount of about 42 to 72% by weight, and wherein said filler is indirectly compressible, granulated, compacted or agglomerated form;
(c) silicon dioxide ranging from about 10 to 30% by weight based on the total weight of the tablet, and wherein said silicon dioxide covers the surface of said filler, and optionally an effervescent couple.

2. The pharmaceutical composition according to claim 1, wherein said active agent is a water-soluble or water insoluble pharmaceutical agent.

3. The pharmaceutical composition according to claim 2, wherein said active pharmaceutical agent is olanzapine, risperidone, loperamide, loratadine, hydrochlorothiazide, donepezil, ondansetron, clonazepam, clozapine, mitrazapine, oxcarbazapine, tramadol, cetirizine, lamotrizine, alprazolam, rizatriptan, zolmitriptan, montelukast, desloratadine or paracetamol or their pharmaceutical acceptable salt or solvate.

4. The pharmaceutical composition according to claim 1, wherein the amount of said filler is about 48 to 58% by weight.

5. The pharmaceutical composition according to claim 1, wherein said filler is mannitol, dextrates, sorbitol, xylitol, sucrose, fructose, lactitol, erythritol or maltitol.

6. The pharmaceutical composition according to claim 5, wherein said filler is mannitol.

7. The pharmaceutical composition according to claim 1, wherein the silicon dioxide is used in an amount of about 10 to 20% by weight.

8. The pharmaceutical composition according to claim 1, wherein said effervescent couple is citric acid (anhydrous)/ sodium hydrogen carbonate.

9. The pharmaceutical composition according to claim 1, wherein said effervescent couple is used in an amount of about 5 to 20% by weight.

10. The pharmaceutical composition according to claim 1, wherein the pharmaceutical composition dissolves in the mouth in 60 seconds or less.

11. The pharmaceutical composition according to claim 1, wherein said composition further comprises a disintegrant, surfactant, lubricant, antiadherant, glidant, sweetener or flavoring agent.

12. The pharmaceutical composition according to claim 11, wherein said disintegrant is polacrilin potassium, microcrystalline cellulose, low substituted hydroxypropyl cellulose, carboxymethyl cellulose, croscarmellose sodium, sodium starch glycolate or crospovidone (crosslinked polyvinylpyrrolidone).

13. The pharmaceutical composition according to claim 12, wherein said disintegrant is crosslinked polyvinylpyrrolidone or polacrilin potassium or a combination thereof.

14. The pharmaceutical composition according to claim 12, wherein said disintegrant is used in an amount of about 10 to 30% by weight.

15. The pharmaceutical composition according to claim 11, wherein said surfactant is sodium lauryl sulphate, polysorbate 80, polysorbate 60, polysorbate 40, polysorbate 20, poloxamers or glyceryl monostearate.

16. The pharmaceutical composition according to claim 15, wherein said surfactant is sodium lauryl sulphate.

17. The pharmaceutical composition according to claim 15, wherein said surfactant is used in an amount of about 1 to 4% by weight.

18. The pharmaceutical composition according to claim 11, wherein said lubricant is sodium stearyl fumarate, glyceryl behenate, calcium stearate, magnesium stearate or stearic acid.

19. The pharmaceutical composition according to claim 18, wherein said lubricant is sodium stearyl fumarate.

20. The pharmaceutical composition according to claim 18, wherein said lubricant is used in an amount of about 1 to 5% by weight.

21. The pharmaceutical composition according to claim 11, wherein said sweetening agent is aspartame, saccharin and salts thereof, acesulfame potassium, sucralose, sucrose or fructose.

22. The pharmaceutical composition according to claim 21, wherein said sweetener is aspartame.

23. The pharmaceutical composition according to claim 21, wherein said sweetener is used in an amount of about 1 to 5% by weight.

24. The pharmaceutical composition according to claim 11, wherein said flavoring agent is grape fruit, cream vanilla, black currant, orange flavor, strawberry, cherry, peppermint or caramel.

25. The pharmaceutical composition according to claim 24, wherein said flavoring agent is strawberry, cherry or orange or a combination thereof.

26. The pharmaceutical composition according to claim 24, wherein said flavoring agent is used in an amount of about 1 to 5% by weight.

27. The pharmaceutical composition according to claim 11, wherein said glidant or antiadherant is talc, magnesium silicate, colloidal silicon dioxide, amorphous silicon dioxide or calcium silicate.

28. The pharmaceutical composition according to claim 27, wherein said glidant or antiadherant is colloidal silicon dioxide or amorphous silicon dioxide or a combination thereof.

29. The pharmaceutical composition according to claim 27, wherein said glidant or antiadherant is used in an amount of 0.5 to 2.0% by weight.

30. The pharmaceutical composition according to claim 1, wherein said silicon dioxide is colloidal silicon dioxide or amorphous silicon dioxide or a combination thereof.

31. A process for preparing an orally disintegrating compressed tablet composition comprising the steps of:

(a) preparing granules of an active ingredient along with silicon dioxide and a conventional excipient, wherein the amount of silicon dioxide is about 10 to 30% by weight based on the total weight of the tablet;
(b) mixing the granules as obtained in step (a) with a filler and a conventional excipient so that said silicon dioxide covers the surface of said filler, wherein the particle size of said filler is 150 microns or above, and the amount of said filler used is about 42 to 72% by weight, wherein said filler is in the directly compressible, granulated, compacted or agglomerated form; and
(c) compressing the blend as obtained in step (b) to form an orally disintegrating compressed tablet.

32. An orally disintegrating compressed tablet consisting essentially of:

(a) an active pharmaceutical agent;
(b) a filler having an average particle size of 150 microns or above, in an amount of about 42 to 72% by weight, and wherein said filler is indirectly compressible, granulated, compacted or agglomerated form;
(c) silicon dioxide ranging from about 10 to 30% by weight based on the total weight of the tablet, wherein said silicon dioxide covers the surface of said filler, and optionally an effervescent couple.

33. A process for preparing an orally disintegrating compressed tablet composition consisting essentially of the steps of:

(a) preparing granules of an active ingredient along with silicon dioxide and a conventional excipient, wherein the amount of silicon dioxide is about 10 to 30% by weight based on the total weight of the tablet;
(b) mixing the granules as obtained in step (a) with a filler and a conventional excipient so that said silicon dioxide covers the surface of said filler, wherein the particle size of said filler is 150 microns or above, and the amount of said filler used is about 42 to 72% by weight, wherein said filler is in the directly compressible, granulated, compacted or agglomerated form; and
(c) compressing the blend as obtained in step (b) to form an orally disintegrating compressed tablet.

* * * * *